(12) United States Patent
Haese et al.

(10) Patent No.: US 7,560,594 B2
(45) Date of Patent: Jul. 14, 2009

(54) METHOD FOR PRODUCING TRIETHANOLAMINE

(75) Inventors: Frank Haese, Bollingstedt (DE); Johann-Peter Melder, Böhl-Iggelheim (DE); Roman Dostalek, Neuleiningen (DE); Manfred Julius, Limburgerhof (DE)

(73) Assignee: BASF Aktiengesellschaft (DE)

( * ) Notice: Subject to any disclaimer, the term of this patent is extended or adjusted under 35 U.S.C. 154(b) by 208 days.

(21) Appl. No.: 11/574,941

(22) PCT Filed: Aug. 10, 2005

(86) PCT No.: PCT/EP2005/008679

§ 371 (c)(1),
(2), (4) Date: Mar. 8, 2007

(87) PCT Pub. No.: WO2006/027077

PCT Pub. Date: Mar. 16, 2006

(65) Prior Publication Data

US 2007/0270615 A1    Nov. 22, 2007

(30) Foreign Application Priority Data

Sep. 9, 2004   (DE) .................. 10 2004 044 091

(51) Int. Cl.
*C07C 209/90* (2006.01)
*C07C 209/84* (2006.01)

(52) U.S. Cl. ...................... 564/497; 564/498
(58) Field of Classification Search ............... None
See application file for complete search history.

(56) References Cited

U.S. PATENT DOCUMENTS

| 3,207,790 | A |   | 9/1965 | Glew et al. |
| 3,387,934 | A |   | 6/1968 | Minklei |
| 4,440,880 | A | * | 4/1984 | Albanesi et al. ............. 523/205 |
| 4,564,461 | A | * | 1/1986 | Skold et al. ................. 508/250 |
| 4,567,303 | A |   | 1/1986 | Boettger et al. |
| 5,545,757 | A |   | 8/1996 | Hammer et al. |
| 6,291,715 | B1 |  | 9/2001 | Ruider et al. |
| 6,323,371 | B2 |  | 11/2001 | Ruider et al. |
| 6,388,137 | B1 |  | 5/2002 | Ruider et al. |

FOREIGN PATENT DOCUMENTS

| EP | 4 015 | 9/1979 |
| EP | 36 152 | 9/1981 |
| EP | 673 920 | 9/1995 |
| EP | 1 081 130 | 3/2001 |
| EP | 1 132 371 | 9/2001 |
| WO | WO 00/32553 | 6/2000 |

OTHER PUBLICATIONS

Mosher, E. et al., "The Chemical Control of Phosphine Gas Generation During the Machining of Nodular Cast Iron", Lubrication Engineering 45(7) (1989), pp. 445-450.

* cited by examiner

*Primary Examiner*—Brian J Davis
(74) *Attorney, Agent, or Firm*—Connolly Bove Lodge & Hutz LLP

(57) ABSTRACT

Method of producing triethanolamine where a phosphane or a compound which liberates a phosphane is added to the triethanolamine.

24 Claims, No Drawings

METHOD FOR PRODUCING TRIETHANOLAMINE

RELATED APPLICATIONS

This application is a national stage application (under 35 U.S.C. 371) of PCT/EP2005/008679 filed Aug. 10, 2005, which claims the benefit of German application 10 2004 044 091.3 filed Sep. 9, 2004.

DESCRIPTION

The present invention relates to a method of producing triethanolamine and to triethanolamine comprising one or more specific phosphorus-containing compounds.

Important fields of use of triethanolamine (TEOA) or its secondary products are, for example, soaps, detergents and shampoos in the cosmetics industry and also dispersants and emulsifiers.

For these and other fields of use, water-clear, colorless triethanolamine with the slightest possible discoloration, e.g. measured as APHA or Gardner color number, which retains these properties even over prolonged storage periods (of e.g. 6, 12 or more months) is desired.

A known problem is that a pure TEOA obtained by fractional distillation of a triethanolamine crude product which has been obtained, for example, by reacting ammonia with ethylene oxide has a yellowish to brownish or pink discoloration (color number e.g. about 10 to 500 APHA in accordance with DIN ISO 6271 (=Hazen)). This discoloration arises particularly in processes in which high temperatures are passed through.

During storage of the alkanolamine, even in a sealed pack and with the exclusion of light, this discoloration is further intensified. (See e.g.: T. I. MacMillan, Ethylene Oxide Derivatives, report No. 193, chapter 6, pages 6-5 and 6-9 to 6-13, 1991, SRI International, Menlo Park, Calif. 94025;

G. G. Smirnova et al., J. of Applied Chemistry of the USSR 61, pp. 1508-9 (1988), and Chemical & Engineering News 1996, Sept. 16, page 42, middle column).

The literature describes various methods of producing triethanolamine with improved color quality.

EP-A-36 152 and EP-A-4015 (both BASF AG) explain the influence of the materials used in methods of producing alkanolamines on the color quality of the process products and recommend nickel-free and/or low-nickel steels.

U.S. Pat. No. 3,207,790 (Dow Chemical Company) describes a method of improving the color quality of alkanolamines by adding a boron hydride of an alkali metal.

EP-A-1 081 130 (BASF AG) relates to a method of producing alkanolamines with improved color quality by treating the alkanolamine with hydrogen in the presence of a hydrogenation catalyst.

EP-A-4015 (BASF AG) describes that mono-, di- and triethanolamine with less discoloration are obtained by adding phosphorous or hypophosphorous acid or derivatives thereof before or during or directly after the stepwise reaction of ethylene oxide with ammonia and subsequent isolation by distillation.

WO-A-00/32553 (BASF AG) relates to a method of purifying TEOA produced by the reaction of aqueous ammonia with ethylene oxide in liquid phase under pressure and at elevated temperature by separating off excess ammonia, water and monoethanolamine from the reaction product, reacting the crude product obtained in this way with ethylene oxide and then rectifying it in the presence of phosphorous or hypophosphorous acid or compounds thereof.

EP-A-1 132 371 (BASF AG) relates to a method of producing alkanolamines with improved color quality where the alkanolamine is treated with an effective amount of phosphorous or hypophosphorous acid or compounds thereof firstly at elevated temperature over a period of at least 5 min (step a) and is then distilled in the presence of an effective amount of one of these phosphorus compounds (step b).

The earlier German patent application No. 102004042453.5 from Aug. 31, 2004 (BASF AG) relates to a method of producing triethanolamine where phosphorous and/or hypophosphorous acid and a basic compound chosen from alkali metal hydroxide, alkaline earth metal hydroxide and [$R^1R^2R^3$(2-hydroxyethyl)ammonium] hydroxide, where $R^1$, $R^2$ and $R^3$, independently of one another, are $C_{1-30}$-alkyl or $C_{2-10}$-hydroxyalkyl, are added to the triethanolamine and in the case of alkali metal hydroxide as basic compound the molar ratio of acid(s):hydroxide is in the range from 1:0.1 to 1:1 and in the case of alkaline earth metal hydroxide as basic compound the molar ratio of acid(s):hydroxide is in the range from 1:0.05 to 1:0.5.

The object of the present invention was to provide a method of producing triethanolamine with good color quality which is improved compared with the prior art. The method is intended to reduce the discoloration of TEOA, e.g. measured as APHA color number, and improve the color stability (undesired increase in the color number over the storage period). In particular, the method was to produce higher yields of TEOA compared with the methods of the applications EP-A-4015, WO-A-00/32553 and EP-A-1 132 371.

Accordingly, a method of producing triethanolamine has been found wherein a phosphane and/or a compound which liberates a phosphane is added to the triethanolamine.

In addition, triethanolamine comprising a phosphane and/or a compound which liberates a phosphane has been found.

Preferred embodiments of the method and of the triethanolamine are given in dependent claims 2 to 13 and 15 to 21.

According to the invention, it has been recognized that while retaining or even improving the color quality compared with the methods of the prior art, the addition according to the invention of phosphorus compound(s) significantly reduces the formation of by-products in the TEOA. At the same time, the TEOA distillation yield is increased. The reduced by-product formation is presumably based on the nonacidic or less acidic effect of the phosphorus compounds, i.e. of the phosphane and/or of the compound which liberates a phosphane.

If a phosphane is added, no problems as a result of salt formation advantageously arise.

Moreover, compared with the known methods using phosphorous or hypophosphorous acid or compounds thereof as additive, it is possible to use smaller amounts of phosphane and/or compound which liberates a phosphane for the same effect.

The triethanolamine used in the method according to the invention can be obtained by known methods, in particular by reacting ammonia with ethylene oxide (e.g. as in EP-A-673 920 or WO-A-00/32553).

The purity of the triethanolamine used in the method according to the invention is preferably greater than 70% by weight, in particular greater than 80% by weight. Besides distilled or undistilled crude triethanolamine, which can also be removed directly in crude form from a plant for producing alkanolamine from the corresponding precursors, it is also possible to use distilled TEOA with a purity of greater than 90% by weight, e.g. greater than 95% by weight, particularly $\geq$97% by weight, in particular $\geq$98% by weight, very particularly $\geq$99% by weight.

It is also possible to use mixtures of triethanolamine with other alkanolamines, such as, for example, monoethanolamine (MEA), diethanolamine (DEA), aminodiglycol (ADG, $H_2NCH_2CH_2OCH_2CH_2OH$), O,N,N-tris(2-hydroxyethyl) ethanolamine, N-(2-aminoethyl)ethanolamine (AEEA), N-(2-hydroxyethyl)piperazine, N-(2-hydroxyethyl)morpholine, N,N'-bis(2-hydroxyethyl)piperazine, monoisopropanolamine, diisopropanolamine, triisopropanolamine and 1,3-propanolamine, or solutions of triethanolamine in an inert solvent, such as, for example, alcohols (methanol, ethanol, isopropanol, n-propanol, n-butanol, 2-ethylhexanol), ethers (tetrahydrofuran, 1,4-dioxane), hydrocarbons (benzene, pentane, petroleum ether, toluene, xylene, hexane, heptane, mihagol) and water or mixtures thereof.

The APHA color number of the triethanolamine used is preferably $\leq 100$, in particular $\leq 50$, very particularly $\leq 20$, e.g. 2 to 15.

The method according to the invention can be carried out as follows:

In a suitable container, e.g. stirred container, which may be equipped with a reflux condenser, an effective amount of phosphane and/or of a compound which liberates a phosphane is/are added to the triethanolamine whose color quality is to be improved in liquid phase, optionally in the presence of an inert solvent, advantageously with stirring or circulation pumping.

Gaseous $PH_3$ can be introduced into the TEOA, for example, via a feed tube.

The mixture is heated over a period of preferably at least 5 min, in particular at least 10 min (for example 10 min to 50 hours, in particular 10 min to 24 hours), very particularly at least 15 min (for example 15 min to 6 hours), particularly preferably at least 30 min (for example 30 min to 4 hours or 40 min to 3 hours or 60 min to 2 hours) at a temperature in the range from 40 to 250° C., in particular 70 to 240° C., very particularly 100 to 230° C., particularly preferably 120 to 220° C., e.g. 150 to 200° C.

Advantageously, the temperatures are preferably lower than when using phosphorous or hypophosphorous acid or compounds thereof as additive according to the prior art.

The phosphane which is added directly and/or is liberated from the compound added (vide infra) is a phosphorus-hydrogen compound.

The phosphanes preferably have the general formula $P_nH_{n+2}$, where n=1 to 9, preferably n=1, 2, 3 or 4, or $P_mH_m$, where m=1 to 9.

The phosphane which is either added directly and/or is liberated from the compound added is particularly preferably $PH_3$ (monophosphane), $P_2H_4$ (diphosphane) or $P_4H_6$ (tetraphosphane), in particular $PH_3$.

The phosphanes can be prepared by known methods (cf. e.g. Römpp Chemie-Lexikon, 10edition, volume 4, page 3275-6 and literature cited therein) and some are also commercially available, such as e.g. $PH_3$.

The phosphorus-containing compound which liberates a phosphane is, for example, a phosphonium halide, $PH_4X$, where X=Cl, Br or I.

Preferably, the compound which liberates a phosphane is a phosphide, in particular a metal phosphide. In these compounds, the phosphorus has the oxidation state-III.

The metal of the metal phosphide is in particular a metal of groups IA, IIA, IIIA or IIB of the Periodic Table of the Elements.

In particular, the metal phosphide is lithium phosphide ($Li_3P$), sodium phosphide ($Na_3P$), potassium phosphide ($K_3P$), magnesium phosphide ($Mg_3P_2$), calcium phosphide ($Ca_3P_2$), aluminum phosphide (AlP), indium phosphide (InP) or zinc phosphide ($Zn_3P_2$).

The liberation of $PH_3$ from metal phosphides is described, for example, in

H.-G. von Schnering in A. L. Rheingold, 'Homoatomic Rings, Chains, and Macromolecules of Main-Group Elements', Elsevier, Amsterdam 1977, pages 317-348, M. Dörnemann and H. Reif, DE-A-36 18 297, R. C. Mariott et al., Inorg. Synth. 1973, 4, pages 1-4, H. W. Hilton, W. H. Robison, J. Agric. Food Chem., 1972, 20, pages 1209-1213, and U.S. Pat. No. 3,387,934 (Oct. 12, 1964, Hooker Chemical Corp.)

The metal phosphides are obtainable by known methods and some are also commercially available.

The compound which liberates a phosphane may of course also be a mixture of compounds, e.g. a mixture of one or more metal phosphides.

The amount of added phosphane and/or added compound which liberates a phosphane is preferably at least 0.001% by weight, e.g. at least 0.01% by weight, in particular 0.02 to 2% by weight, particularly preferably 0.03 to 1.0% by weight, very particularly preferably 0.5 to 0.9% by weight, based on the amount of triethanolamine used (calculated as pure TEOA); however, the effect also arises with larger amounts. If a phosphane and a compound which liberates a phosphane are used together, the above quantitative data refer to both additives together.

In order to improve the handling properties it may be advantageous here to meter in the effective amount of the phosphane and/or of the compound which liberates a phosphane in a suitable inert diluent or solvent, such as, for example, water, alcohols (methanol, ethanol, isopropanol, n-propanol, n-butanol, 2-butanol, pentanols, hexanols), ethers (tetrahydrofuran, 1,4-dioxane) or an alkanolamine (e.g. an ethanolamine, such as monoethanolamine, diethanolamine, N-(2-aminoethyl)ethanolamine, in particular triethanolamine), in the form of a, for example, 1 to 40% strength by weight, particularly 5 to 30% strength by weight, in particular 10 to 20% strength by weight, solution or suspension.

The required treatment time of the triethanolamine with the addition or the additions arises inter alia from the degree of discoloration of the triethanolamine used and the extent of desired decoloration and/or color stability of the TEOA. For a given temperature generally the higher the degree of discoloration of the triethanolamine used in the process according to the invention and the higher the requirements placed on the color quality of the process product, the greater the time.

The temperature must, however, not be chosen to be too high, i.e. generally not higher than 250° C. since otherwise a degradation of the triethanolamine can take place which adversely affects the color quality of the TEOA ultimately obtained. The temperatures and treatment times which are most favorable for the particular triethanolamine used are easy to ascertain in simple preliminary experiments.

During this treatment of the triethanolamine with the phosphane and/or the compound which liberates a phosphane it is advantageous if the mixture is further mixed (e.g. stirred or circulated by pump) throughout the entire treatment time or at intervals.

It is also advantageous if the treatment of the triethanolamine is carried out under a protective gas atmosphere (e.g. $N_2$ or Ar), i.e. in the absence of $O_2$.

The treatment of the alkanolamine with the phosphane and/or the compound which liberates a phosphane can also be carried out continuously in suitable containers, e.g. in a tubular reactor or in a cascade of stirred containers.

The treatment of the triethanolamine with the phosphane and/or the compound which liberates a phosphane can be carried out advantageously in the bottoms container of a distillation column or in a distillation initial charge vessel before and/or during the distillation of the triethanolamine.

In a particular embodiment during the treatment of the triethanolamine with the phosphane and/or the compound which liberates a phosphane, an inert gas (e.g. $N_2$ or Ar) is passed as a stripping stream through the triethanolamine in order to remove from the mixture any low-boiling components which form and which can have an adverse effect on the color quality, such as, for example, acetaldehyde or secondary products thereof.

In another particular embodiment, the triethanolamine to be treated is circulated in liquid form via a heat exchanger and any low-boiling components which form, which can have an adverse effect on the color quality, such as, for example, acetaldehyde, are removed in the process.

The heat exchanger here may be an open heat exchanger, such as, for example, a falling-film or wiper-blade evaporator, or a sealed heat exchanger, such as, for example, a plate- or tube-bundle heat exchanger.

Depending on the reaction conditions chosen, it may be necessary to carry out the treatment of the triethanolamine with the phosphane and/or the compound which liberates a phosphane at a superatmospheric pressure (e.g. 0.1 to 50 bar) in order to avoid the undesired escape of one or more components from the mixture.

In a particularly preferred embodiment of the method according to the invention, the treatment of the triethanolamine with the phosphane and/or the compound which liberates a phosphane is carried out in the presence of water, particularly if a metal phosphide is used as compound which liberates a phosphane.

The water content of the triethanolamine is preferably in the range from 0.01 to 20% by weight, in particular in the range from 0.02 to 10% by weight, very particularly in the range from 0.03 to 5% by weight, such as, for example, in the range from 0.04 to 2% by weight, in each case based on the pure triethanolamine.

The water is added to the TEOA used in the method according to the invention and/or the TEOA already contains water, e.g. caused as a result of the preceding TEOA production stage.

The distillation or rectification of the triethanolamine to separate off the addition or the additions takes place discontinuously or continuously at a pressure of usually less than 100 mbar (100 hPa), for example at about 10 to 50 mbar or 1 to 20 mbar, preferably at 0.5 to 5 mbar, and at bottoms temperatures of generally 100 to 250° C., where in the case of the continuous procedure, in a particular embodiment, any low-boiling component fractions present are drawn off overhead and the TEOA is obtained in the side take-off.

The residue of the distillation or rectification comprising the added compound(s) and/or reaction products thereof can, in a particular embodiment, be completely or partially returned to the distillation process.

The method according to the invention produces a triethanolamine with improved color quality which, directly after being obtained, has an APHA color number in the range from 0 to 30, in particular from 0 to 20, very particularly from 0 to 10, e.g. 1 to 6.

All of the APHA data in this document are in accordance with DIN ISO 6271 (=Hazen). All of the ppm data in this document are based on the weight (ppm by weight).

We claim:

1. A method of producing triethanolamine which comprises adding a phosphane and/or a compound which liberates a phosphane to the triethanolamine.

2. The method according to claim 1, wherein the phosphane is $PH_3$, $P_2H_4$ or $P_4H_6$.

3. The method according to claim 1, wherein the compound which liberates a phosphane is a metal phosphide.

4. The method according to claim 1, wherein the phosphane and/or the compound which liberates a phosphane is added to the triethanolamine before and/or during distillation of the triethanolamine.

5. The method according to claim 1, wherein the triethanolamine is treated with the addition over a period of at least 5 minutes.

6. The method according to claim 1, wherein the triethanolamine is treated with the addition over a period in the range from 10 minutes to 50 hours.

7. The method according to claim 6, wherein the treatment of the triethanolamine with the addition is carried out at a temperature in the range from 40 to 250° C.

8. The method according to claim 1, wherein 0.001 to 2% by weight (based on the pure triethanolamine) of the phosphane and/or of the compound which liberates a phosphane is added to the triethanolamine.

9. The method according to claim 3, wherein the phosphide is a phosphide of a metal of groups IA, IIA, IIIA or IIB of the Periodic Table of the Elements.

10. The method according to claim 3, wherein the phosphide is lithium phosphide, sodium phosphide, potassium phosphide, magnesium phosphide, calcium phosphide, aluminum phosphide, indium phosphide or zinc phosphide or a mixture thereof.

11. The method according to claim 1, wherein the triethanolamine comprises water.

12. The method according to claim 1, wherein the triethanolamine comprises water in the range from 0.01 to 20% by weight (based on the pure triethanolamine).

13. The method according to claim 1, wherein the triethanolamine comprises at least 0.001% by weight (based on the pure triethanolamine) of the phosphane and/or of the compound which liberates a phosphane.

14. A triethanolamine which comprises at least 0.001% by weight (based on pure triethanolamine) of phosphane and/or of a compound which liberates a phosphane.

15. The triethanolamine according to claim 14, wherein the phosphane is $PH_3$, $P_2H_4$ or $P_4H_6$.

16. The triethanolamine according to claim 14, wherein the compound which liberates a phosphane is a metal phosphide.

17. The triethanolamine according to claim 16, wherein the metal of the phosphide is a metal of groups IA, IIA, IIIA or IIB of the Periodic Table of the Elements.

18. The triethanolamine according to claim 16, wherein the metal phosphide is lithium phosphide, sodium phosphide, potassium phosphide, magnesium phosphide, calcium phosphide, aluminum phosphide, indium phosphide or zinc phosphide or a mixture thereof.

19. The triethanolamine according to claim 14, wherein the triethanolamine comprises 0.001 to 2% by weight (based on the pure triethanolamine) of the phosphane and/or of the compound which liberates a phosphane.

20. The triethanolamine according to claim 14, wherein the triethanolamine comprises water.

21. The triethanolamine according to claim 14, wherein the triethanolamine comprises water in the range from 0.01 to 20% by weight (based on the pure triethanolamine).

22. The method according to claim 1, wherein the triethanolamine produced has an APHA color number in the range from 0 to 30.

23. A triethanolamine which comprises triethanolamine and phosphane and/or a compound which liberates a phosphane and an APHA color number in the range from 0 to 30.

24. The triethanolamine according to claim 23, wherein the APHA color number is in the range from 1 to 6.

* * * * *